United States Patent
Burks et al.

(10) Patent No.: US 10,161,242 B2
(45) Date of Patent: Dec. 25, 2018

(54) COLUMN FLOW TESTING

(71) Applicant: HALLIBURTON ENERGY SERVICES, INC., Houston, TX (US)

(72) Inventors: Jody Marie Burks, Spring, TX (US); Denise Nicole Benoit, Houston, TX (US); Chandra Sekhar Palla-Venkata, Sugar Land, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/119,296

(22) PCT Filed: Mar. 28, 2014

(86) PCT No.: PCT/US2014/032262
§ 371 (c)(1),
(2) Date: Aug. 16, 2016

(87) PCT Pub. No.: WO2015/147880
PCT Pub. Date: Oct. 1, 2015

(65) Prior Publication Data
US 2017/0003210 A1 Jan. 5, 2017

(51) Int. Cl.
*G01N 11/06* (2006.01)
*E21B 47/10* (2012.01)
*G01N 33/28* (2006.01)

(52) U.S. Cl.
CPC .............. *E21B 47/10* (2013.01); *G01N 11/06* (2013.01); *G01N 33/2823* (2013.01)

(58) Field of Classification Search
CPC .......................... G01N 33/2823; G01N 11/06
See application file for complete search history.

(56) References Cited

U.S. PATENT DOCUMENTS

| 4,817,423 | A | * | 4/1989 | Christiansen | ........ G01N 33/241 73/152.05 |
| 5,297,420 | A | * | 3/1994 | Gilliland | ................ G01N 15/08 73/38 |
| 2004/0094298 | A1 | | 5/2004 | Tare et al. | |
| 2005/0019951 | A1 | * | 1/2005 | Gjerde | .................. B01J 20/285 436/177 |
| 2006/0225523 | A1 | | 10/2006 | Reddy et al. | |
| 2008/0162056 | A1 | * | 7/2008 | Greaves | ................ E21B 43/006 702/24 |
| 2008/0178683 | A1 | | 7/2008 | Heathman et al. | |
| 2009/0241700 | A1 | | 10/2009 | Haggerty et al. | |

(Continued)

OTHER PUBLICATIONS

International Search Report and Written Opinion; PCT Application No. PCT/US2014/032262; dated Dec. 24, 2014.

*Primary Examiner* — Lisa Caputo
*Assistant Examiner* — Alex Devito
(74) *Attorney, Agent, or Firm* — Polsinelli PC

(57) ABSTRACT

System and method for monitoring frac fluid flow through a column bed includes preparing a vessel (112, 440) with a column including a filtering member (120, 420), a column bed (114, 414) simulating a downhole environment, and a frac fluid (116, 416). Frac fluid (116, 416) is flowed through the column bed (114, 414) at an acceleration exceeding gravity for a predetermined period of time. The amount of liquid that flows through the column bed (114, 414) and that is recovered after the predetermined period of time is then determined.

21 Claims, 7 Drawing Sheets

(56) References Cited

U.S. PATENT DOCUMENTS

2011/0295509 A1 12/2011 Huynh et al.
2013/0125630 A1* 5/2013 Collins ................ E21B 43/20
                73/64.56

* cited by examiner

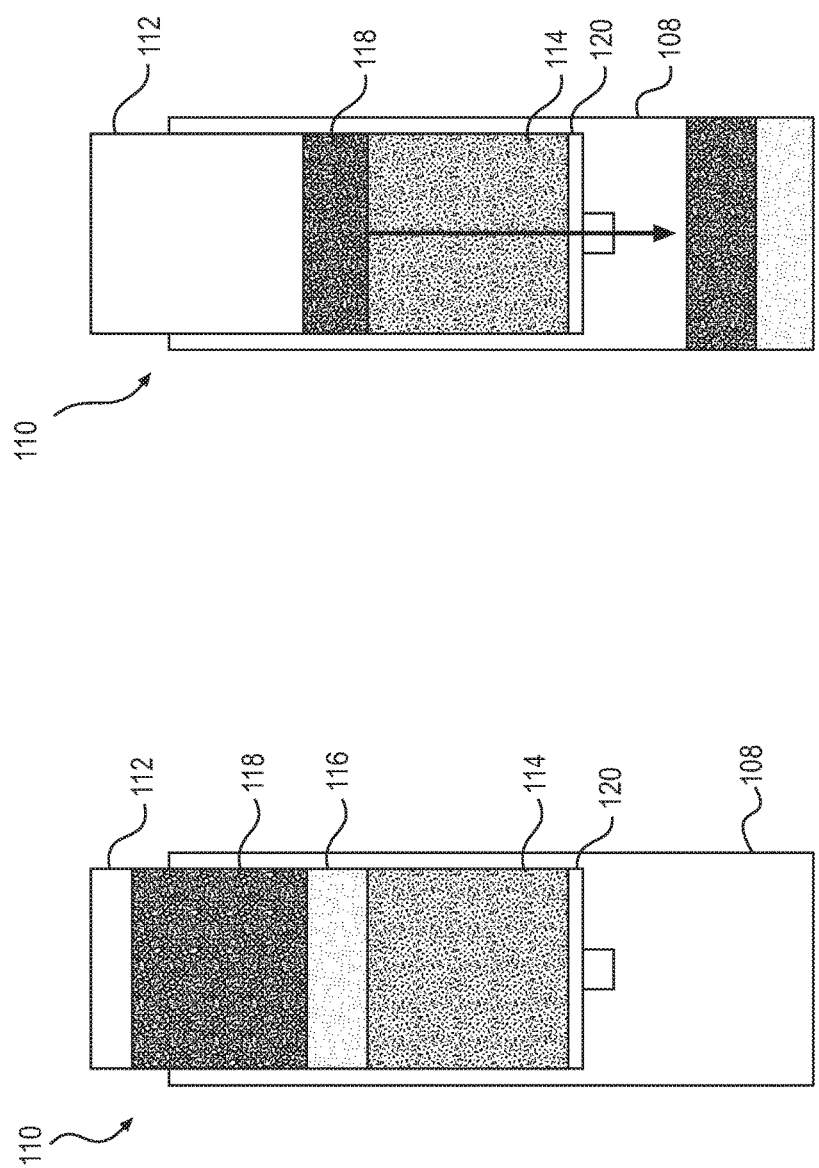

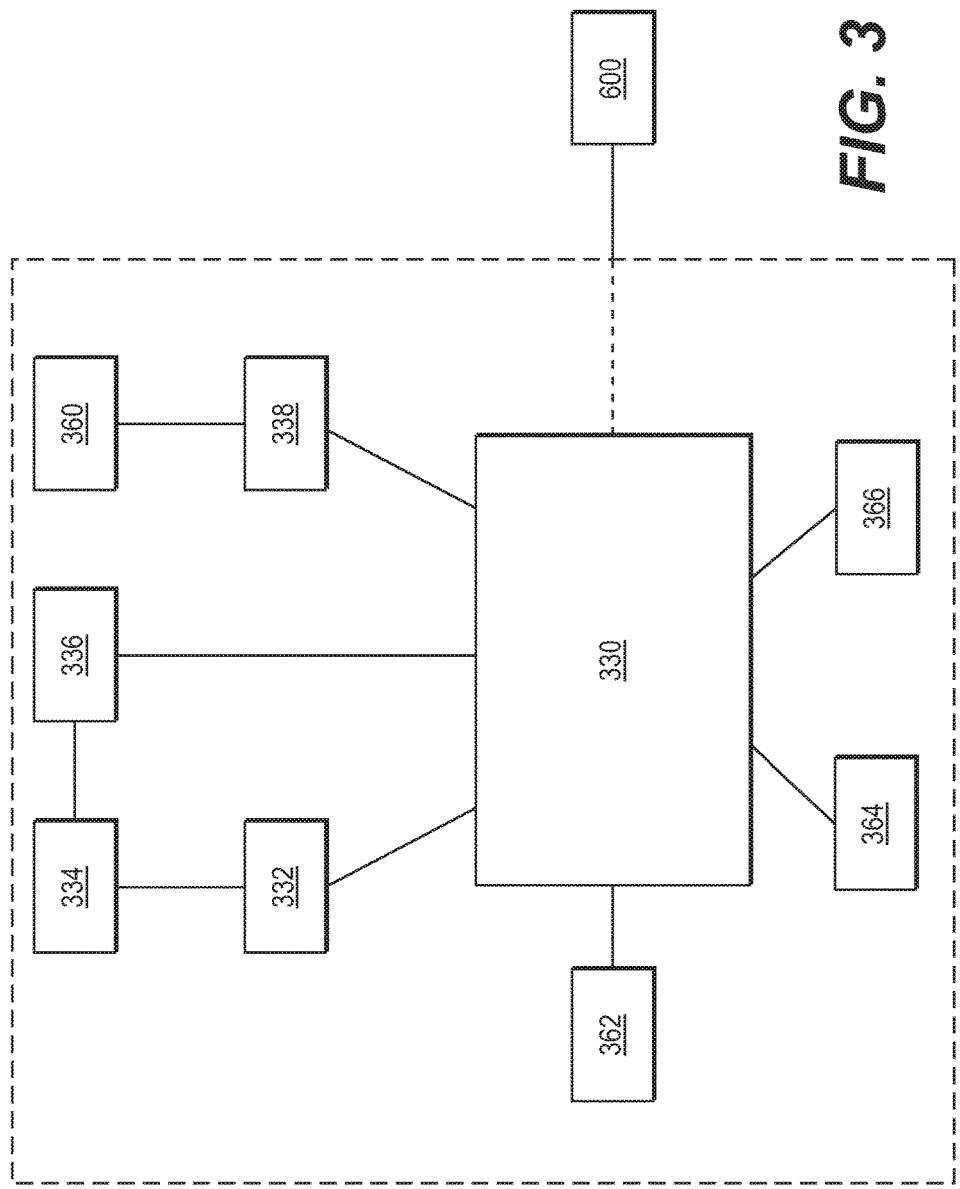

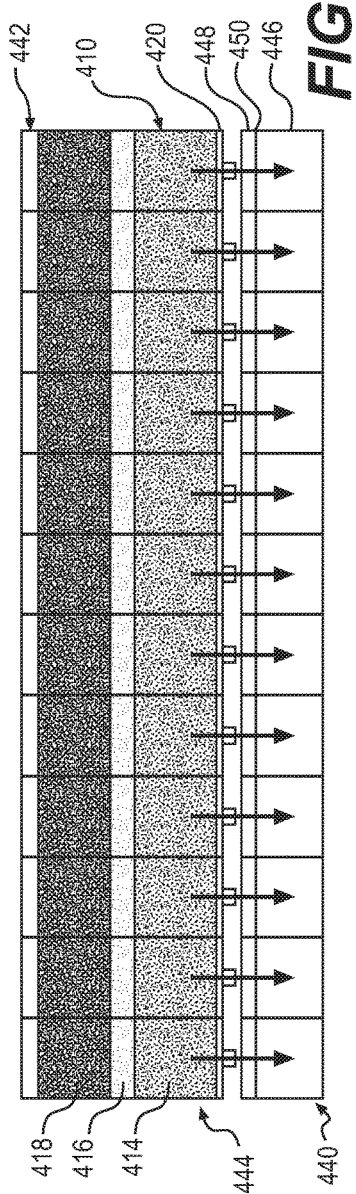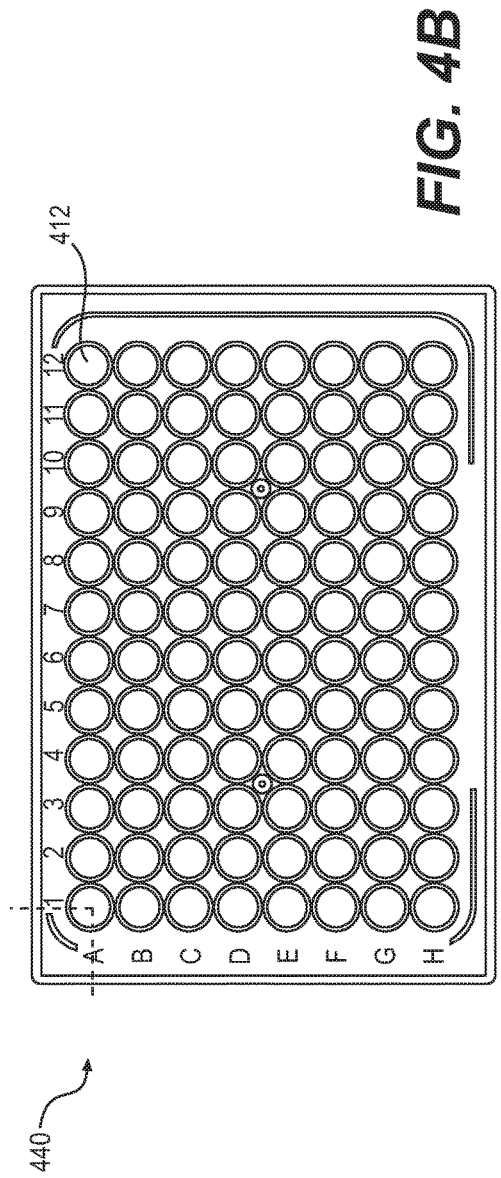

COLUMN FLOW TESTING

CROSS-REFERENCE TO RELATED APPLICATIONS

This application is a national stage entry of PCT/US2014/032262 filed Mar. 28, 2014, said application is expressly incorporated herein in its entirety.

FIELD

The present disclosure relates to column flow testing and, more particularly, to devices and methods for column flow testing for measuring fluid recovery.

BACKGROUND

During oil and gas exploration, various fluid components of an operation can be varied to optimize recovery of oil or gas from a well. Testing can be performed prior to an operation in order to optimize the fluid components to be used in the operation. For example, relative to a hydraulic fracturing ("fracking") operation, surfactants and/or fracking fluid components to be used in the operation can be modified based on well conditions in order to customize/optimize the operation.

BRIEF DESCRIPTION OF THE DRAWINGS

Implementations of the present technology will now be described, by way of example only, with reference to the attached figures, wherein:

FIG. 1 is a diagrammatic side view illustration of an exemplary spin column at a first stage of a column flow testing in accordance with the disclosure;

FIG. 2 is a diagrammatic side view illustration of the column of FIG. 1 at a second stage of column flow testing;

FIG. 3 is a schematic illustration of a system for evaluating fluid recovery according to the disclosure;

FIG. 4A is a diagrammatic cross-sectional illustration of an exemplary column flow testing device according to the disclosure;

FIG. 4B is a diagrammatic top view illustration of an exemplary column flow testing device according to the disclosure;

Figure 5:
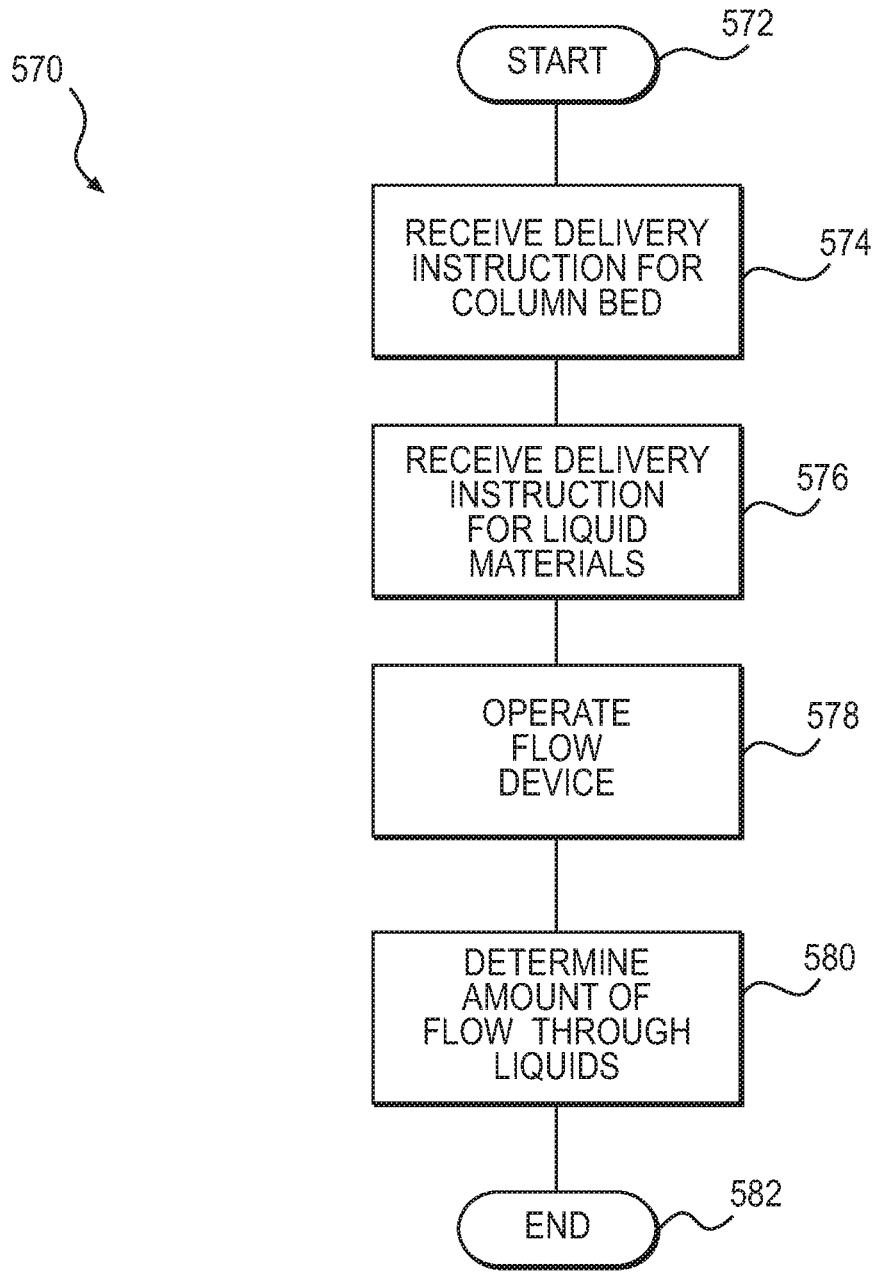
FIG. 5 is a schematic illustration of an exemplary method of evaluating fluid recovery according to the disclosure.

It should be understood that the various embodiments are not limited to the arrangements and instrumentality shown in the drawings.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

In the following description, terms such as "upper," "upward," "lower," "downward," "above," "below," "downhole," "uphole," "longitudinal," "lateral," and the like, as used herein, shall mean in relation to the bottom or furthest extent of, the surrounding wellbore even though the wellbore or portions of it may be deviated or horizontal. Correspondingly, the transverse, axial, lateral, longitudinal, radial, and the like orientations shall mean positions relative to the orientation of the wellbore or tool. Additionally, the illustrated embodiments are depicted so that the orientation is such that the right-hand side is downhole compared to the left-hand side.

Several definitions that apply throughout this disclosure will now be presented. The term "coupled" is defined as connected, whether directly or indirectly through intervening components, and is not necessarily limited to physical connections. The connection can be such that the objects are permanently connected or releasably connected. The term "communicatively coupled" is defined as connected, either directly or indirectly through intervening components, and the connections are not necessarily limited to physical connections, but are connections that accommodate the transfer of data between the so-described components. The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other thing that "substantially" modifies, such that the component need not be exact. For example, substantially cylindrical means that the object resembles a cylinder, but can have one or more deviations from a true cylinder. The terms "comprising," "including" and "having" are used interchangeably in this disclosure. The terms "comprising," "including" and "having" mean to include, but not necessarily be limited to the things so described.

The term "radial" and/or "radially" means substantially in a direction along a radius of the object, or having a directional component in a direction along a radius of the object, even if the object is not exactly circular or cylindrical. The term "axially" means substantially along a direction of the axis of the object. If not specified, the term axially is such that it refers to the longer axis of the object.

An exemplary spin column 110 according to the present disclosure is shown in FIG. 1 that can be used with flow device 330 (FIG. 3), for example, a conventional centrifuge, operable to flow fluid through the spin column 110 with a force that exceeds simple gravity and without high pressure. Alternatively, the flow device 330 can be a vacuum operable to flow fluid through the spin column 110 using vacuum pressure.

As shown in FIG. 1, the spin column 110 includes a vessel 112 for containing a column bed layer 114 and one or more layers 116, 118 of materials. In some embodiments, the vessel 112 can be designed to have flowthrough collected by a centrifuge or micro-centrifuge tube 108, and the flow device 330 can be a conventional centrifuge or micro-centrifuge. In some embodiments, the vessel 112 can be an individual well or one well of a multi-well filter 444 and collection plate 446 with arrangement 440 (FIGS. 4A and 4B). The centrifuge or micro-centrifuge is operable to flow fluid through the spin column 110 with a force due to centripetal acceleration or vacuum pressure.

The spin column unit 110 includes a filtering member 120, for example, a frit or a screen that supports the layers 114, 116, 118. As shown in FIG. 1, the spin column vessel 112 can include a first layer 114 adjacent the filtering member 120 that comprises a medium resistant to fluid flows such as, for example, oilfield fluid flows. The first layer 114 can include, for example, proppant, formation cuttings, a mix of proppant and formation cuttings, resin, or other separatory material. The term "proppant" refers to solid geologic or synthetic (i.e., man-made) materials including, but not limited to, sand, ceramic, other synthetic materials, or the like. The proppant can be in the form of beads or fibers, for example. The spin column vessel 112 includes a second layer 116 comprising, for example, brine, flowback water, or fracturing fluid (frac fluid). The frac fluid can include surfactant or other components. The spin column vessel 112 can include a third layer 118 comprising, for example, crude oil.

The spin column vessel 112 can be placed in the collection vessel 108. It should be appreciated that the components of spin column unit 110 can be prefabricated/pre-made or custom-made, with a desired vessel, filtering member, column bed, and one or more materials to be analyzed. The layers of materials can be commercially pre-made, for example, proppant columns in brine, or loaded by hand using slurries of materials, for example, formation cuttings in frac fluid solution.

In an exemplary operation, the spin column 110 can be prepared by providing the filtering member 120 at a first end of the vessel 112. The column bed layer 114 is layered on the filtering member 120. The column bed layer 114 can be pre-made before being layered on the filtering member or the column bed layer 114 can be prepared in the vessel 112. For example, to prepare the column bed layer 114 in the vessel 112, samples of material, such as, for example, proppant and/or formation cuttings simulating downhole conditions, in fluid such as, for example, brine, frac fluid, or some other determined fluid can be placed in the vessel 112 and centrifuged to an appropriate G-force for a predetermined amount of time to prepare the column bed layer 114. The sample materials can include proppant or rock cuttings that are selected to simulate a well formation to be analyzed. The materials can actually be retrieved from the well to be analyzed or can be chosen based on a prediction of the composition of a well formation to be analyzed. In some embodiments, the column bed layer 114 can be prepared in the vessel 112 by placing proppant and/or formation cuttings simulating downhole conditions into the vessel 112 and layering fluid such as, for example, brine, frac fluid, or some other determined fluid on the column bed layer 14 and allowing the fluid to penetrate the column bed layer by gravity.

After the column bed layer 114 is prepared, a second layer 116 comprising a predetermined amount of fluid, for example, frac fluid, can be applied to the column bed layer 114 and the vessel 112 centrifuged for a short period of time. The term "frac fluid" is generally understood to include KCl, slick water, aqueous or hydrocarbon-based fracturing fluid, or any fluid (including gels) that can be used in hydraulic fracturing. The frac fluid can include an additive or additives such as surfactant, clay stabilizer, biocide, buffers, acids, etc. A collection vessel 108 can receive the vessel 112 and can therefore collect flowthrough fluids that flow through the column bed layer 114. The precise amount of frac fluid collected can be determined by measuring the volume or mass of the flowthrough; that is, the amount of fluid from the second layer 116 that flows through the column bed layer 114 during centrifugation.

A third layer 118, for example, crude oil, can then be applied to the spin column 110, and the sample centrifuged again for a short time, depending on the column materials. The precise amount of oil recovered can be determined by measuring the volume or mass of the recovered oil.

As would be understood by persons skilled in the art, the aforementioned process can be carried out for any number of variations of frac fluid composition, surfactant or other additives, oil composition, and/or proppant and/or formation cuttings. The resulting flowthrough measurements can be compared to determine the most efficient frac fluid and/or surfactant for the formation involved. As long as the rate and duration of centrifugation are maintained constant, this process can provide useful differentiation between various frac fluids and/or surfactants.

In some embodiments, the second layer 116 of frac fluid and the third layer 118 of crude oil can be layered over the same column bed layer 114 for one centrifugation step, rather than using two centrifugation steps. It should be appreciated that the aforementioned processes for preparing the column bed layer 114 and flowing fluid and oil through the column bed layer 114 are exemplary only, and further variations of such processes are contemplated by this disclosure.

These processes can be conducted at room temperature and pressure, or the samples can be incubated at a user-defined temperature representative of downhole conditions. For experiments at higher temperatures, high-temperature, low-speed (non-ultra) centrifuges and larger spin column setups (e.g., 10-40 ml) can be utilized, especially in heated, explosion-resistant centrifuges designed for crude oil testing procedures. In some embodiments, a pre-centrifugation incubation step could also be used with gravity-assisted flow.

It should be appreciated that the previously described processes can use a vacuum flow device to apply an appropriate pressure to flow the fluid or fluid layers through the spin column 110, and the precise amount of fluid flowthrough can be determined. As previously described, the flow device 330 can be a vacuum flow device.

The results of the aforementioned processes can help understand how different fluid components, such as surfactants or other additives, move in and interact with a formation. Such an understanding can enable better prediction of the extent of clean-up procedures necessary to repair formations, allow more specific tailoring of production enhancement services and products to individual wells, and allow a more reliable visual representation or model of how the component and frac fluid are interacting with a particular well formation. The effects of clay stabilizers on rock formation surfaces and how this affects fluid flow can be observed. In addition, interactions and/or compatibility of additives such as biocides and other components can be observed.

Referring now to FIG. 3, a system 300 for evaluating fluid recovery is schematically illustrated. The system 300 can be operated and derivative processes can be performed manually, in a semi-automated manner, or in a fully-automated manner. The system 300 can be associated with a general computing system 600, discussed in more detail below, which can automate or semi-automate one or more features of the system 300 for evaluating fluid recovery. The system 300 for evaluating fluid recovery and/or the general computing system 600 can be constructed for portable and economical transport to field labs or on-site locations.

The system 300 includes a flow device 330, such as a centrifuge, a micro-centrifuge, or a vacuum apparatus. As discussed above, the flow device 330 is operable to flow fluid through one or more spin columns 110, 410 (FIG. 4A), in the case of a centrifuge or micro-centrifuge, with a force due to centripetal acceleration or, in the case of a vacuum, with a force due to vacuum pressure.

System 300 can include a temperature control device 362 capable of varying the temperature of materials or a spin column to be representative of downhole conditions.

The system 300 can include a first delivery arrangement 332 for delivering precompressed pellets to a vessel 112, 412. Alternatively, the first delivery arrangement 332 can deliver, for example, a loose volume of proppant or mixed proppant and/or rock granules (i.e., formation cuttings) the vessel 112, 412. The vessel 412 can be an individual well of a multi-well plate arrangement 440.

Referring to FIGS. 4A and 4B, an example of a conventional multi-well plate arrangement 440 is diagrammatically illustrated. The multi-well plate arrangement 440 includes a plurality of wells 412, such as, for example, 6, 24, 96, or 384 wells per plate. In some embodiments, the plate arrangement 440 includes a top portion 442, a middle portion 444, and a base portion 446. The middle portion 444 houses samples, similar to that described above in connection with vessel 112. That is, the middle portion 444 can include a filtering member 420, for example, a frit or a screen, that supports a spin column 410. As shown in FIG. 4A, the spin column 410 can include a first layer 414 adjacent the filtering member 420 that comprises a medium resistant to fluid flows such as, for example, oilfield fluid flows. The first layer can include, for example, proppant, formation cuttings, a mix of proppant and formation cuttings, resin, or other separatory material. The spin column 410 includes a second layer 416 comprising, for example, brine, flowback water, or frac fluid. The frac fluid can include surfactant and/or another additives. The spin column 410 can include a third layer 418 comprising, for example, crude oil. In some instances the top portion 442 can be a removable cover that can tightly seal the wells 412. It should be appreciated that one or more wells 412 of the plate arrangement 440 can include the same first, second, and/or third layers 414, 416, 418, or each well 412 can have different first, second, and/or third layers 414, 416, 418. The bottom portion 446, for example, a micro titer plate or other arrangement of collection wells, can collect flowthrough fluids that flow through the column bed layer 414. In some embodiments, the bottom portion 446 can be a single piece or a combination of individual wells or groups of wells. In some embodiments, the plate arrangement 440 may only include portions 444 and 446 and be operable without the cover 442. It should be appreciated that one or more of the portions 442, 444, 446 of the plate arrangement 440 can be disposable. The well arrangements of the middle and bottom portions 444, 446 match one another and are alignable to prevent cross-contamination of wells.

In some embodiments, the plate arrangement 440 can include a lower middle portion 448 between the middle portion 444 and the base portion 446. The lower middle portion can include a filtering membrane 450 such as, for example, a hydrophobic membrane, to separate hydrophobic and hydrophilic layers of flowthrough fluid. Alternatively, the filtering membrane 450 can be a hydrophilic membrane. Each well of the lower middle portion 448 has its own separate filter to prevent cross-contamination of wells. It should be appreciated that the lower middle portion 448 of the plate arrangement 440 can be disposable.

Referring again to FIG. 3, in some embodiments, the flow device 330 can centrifuge a loaded multi-well plate arrangement 440 at a user-determined, low relative centrifugal force (rcf) for a user-determined length of time to pull liquid contents through a column bed layer 414. For example, the centrifuge can operate at 50-25,000 rcf for 1 second to 20 minutes. It should be appreciated that operation of the flow device 330 can be varied based on the bed materials, liquid materials, and oil being tested. The centrifuge rotor could be swing-bucket-style with standard microplate acceptor, which applies vertical relative gravitational force during spin, or a fixed-rotor style with 12 or 24 microfuge tube holders.

The system 300 for evaluating fluid recovery can include a precompression arrangement 334 to precompress pellets of proppant/rock samples for consistent weight and compression force and for ease of loading into sample wells 412. The precompression arrangement 334 can store the pellets and make the pellets accessible to the first delivery arrangement 332 for delivery to a well 412. The pellets may be generated in a user-defined sequence and combination, for example, by way of an input to the general computing system 600.

System 300 can include a mixing device 336 capable of mixing and subsequently delivering consistent loose volumes of mixes of proppant and/or rock granules to the precompression arrangement 334 and/or directly to the first delivery arrangement 332. The aliquots of loose volumes can be added in a user-defined sequence and combination, for example, by way of an input to the general computing system 600. When used with a multi-well plate arrangement 440, different mixes or pellets can be sent to different wells. For example, materials simulating a first formation can be sent to one or more wells, and materials simulating a second formation can be sent to one or more different wells.

The system 300 for evaluating fluid recovery can include a second delivery arrangement 338 for delivering a predetermined aliquot of various liquid materials such as, for example, brine, well fresh water, well flowback water, frac fluid base gel, biocides, surfactants, buffers, well crude oil, or the like to one or more aligned wells 412 of the plate arrangement 440. The aliquots can be added in user-defined sequence and combination, for example, by way of an input to the general computing system 600. As an example, one sequence may be: add 0.4 g of 100 mesh sand; then add 100 µl of flowback water; then add a layer of 200 µl of frac fluid mix; then add 200 µl of crude oil sample. Another example may be: add 150 µl of frac fluid mix; then add 0.4 g of 100 mesh sand and formation cuttings mix; then add 400 µl of crude oil sample. Liquid such as brine, flowback water, frac fluid mixes, and the like can be premade or prepared in the second delivery arrangement 338 before dispensing. Each well 412 can receive the same sample order/ratio for repetitions or different order/ratio/contents for comparisons. System 300 can include a mixing and dispensing arrangement 360 that includes one or more containers (not shown) having various pre-made recipes of frac solutions and their components, such as, for example, gelling agents, surfactants, biocides, buffers, and the like for delivery to the multi-well plate arrangement 440 via the second delivery arrangement 338. The dispensing arrangement 360 may also include one or more containers of crude oil for delivery to the multi-well plate arrangement 440 via the second delivery arrangement 338. In some embodiments, the mixing and dispensing arrangement 360 can be capable of preparing frac gel components if necessary.

System 300 can include a monitoring device 364 for monitoring progression of liquid through the spin column 410. The monitoring device can include, for example, an ultrasonic non-contact sensor, an absorbance and/or fluorescence plate reader with path-length determination capability, other devices that utilize crude oil fluorescence or absorbance, float level sensors, or the like. The system 300 can include a detection system 366 capable of measuring flowthrough volume that is collected at the bottom portion 446 after centrifugation or vacuum application. The detection system 366 can be a volume probe, a non-contact sensor, or the like. Alternatively, the detection system 366 can be a mass-based system. The detection system may also be used to determine the ratio of components such as that of fracking fluid flowthrough to crude oil, or concentration of components after flow-through, using absorbance, transmission, fluorescence other measurements. It should be appreciated that other analytical methods or instrumentation can be paired with detection system 366.

Figure 6:
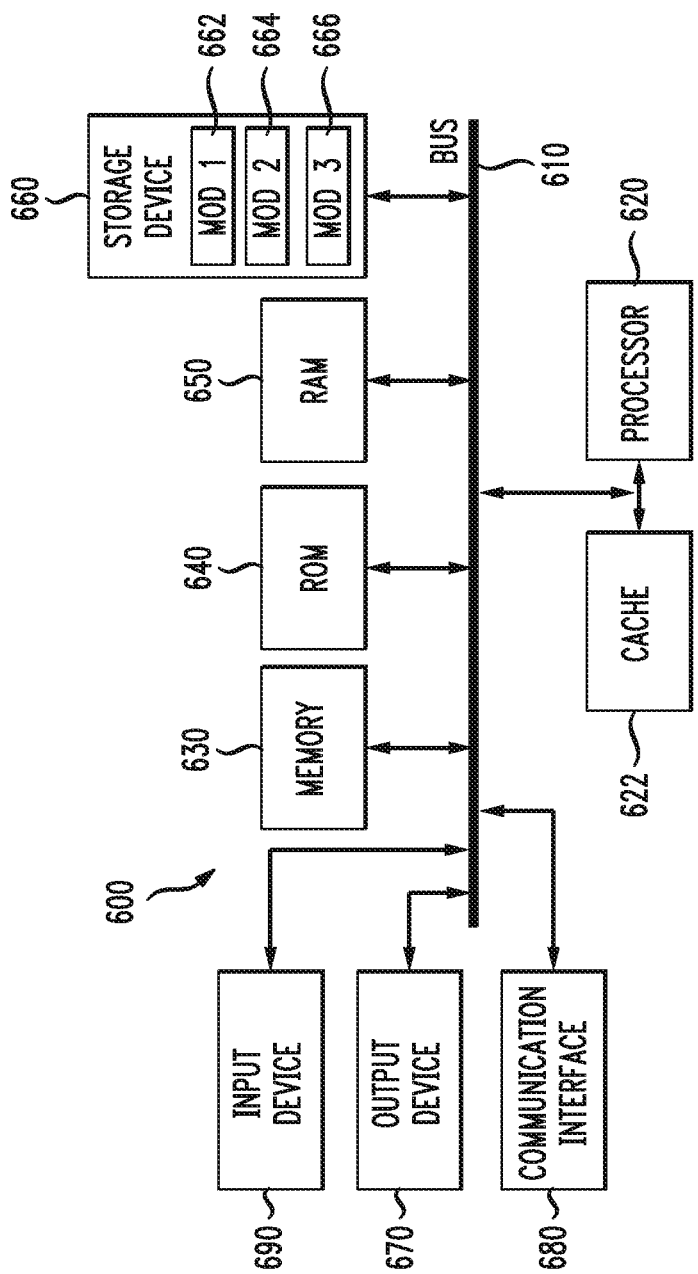
FIG. 6 is a schematic illustration of a general system for implementing principles of the disclosure.

Referring now to FIG. 6, which illustrates a general system 600, all or part of which can be used to implement the principles disclosed herein. With reference to FIG. 6, an exemplary system and/or computing device 600 includes a processing unit (for example, a central processing unit (CPU) or processor) 620 and a system bus 610 that couples various system components, including the system memory 630 such as read only memory (ROM) 640 and random access memory (RAM) 650, to the processor 620. The system 600 can include a cache 622 of high-speed memory connected directly with, in close proximity to, or integrated as part of the processor 620.

The system 600 copies data from the memory 630 and/or the storage device 660 to the cache 622 for quick access by the processor 620. In this way, the cache provides a performance boost that avoids processor 620 delays while waiting for data. These and other modules can control or be configured to control the processor 620 to perform various operations or actions. Other system memory 630 can be available for use as well. The memory 630 can include multiple different types of memory with different performance characteristics. It can be appreciated that the disclosure may operate on a computing device 600 with more than one processor 620 or on a group or cluster of computing devices networked together to provide greater processing capability.

The processor 620 can include any general purpose processor and a hardware module or software module, such as module 1 662, module 2 664, and module 3 666 stored in storage device 660, configured to control the processor 620 as well as a special-purpose processor where software instructions are incorporated into the processor. The processor 620 can be a self-contained computing system, containing multiple cores or processors, a bus, memory controller, cache and the like. A multi-core processor can be symmetric or asymmetric. The processor 620 can include multiple processors, such as a system having multiple, physically separate processors in different sockets, or a system having multiple processor cores on a single physical chip.

Similarly, the processor 620 can include multiple distributed processors located in multiple separate computing devices, but working together such as via a communications network. Multiple processors or processor cores can share resources such as memory 630 or the cache 622, or can operate using independent resources. The processor 620 can include one or more of a state machine, an application specific integrated circuit (ASIC), or a programmable gate array (PGA) including a field PGA.

The system bus 610 can be any of several types of bus structures including a memory bus or memory controller, a peripheral bus, and a local bus using any of a variety of bus architectures. A basic input/output (BIOS) stored in ROM 640 or the like, may provide the basic routine that helps to transfer information between elements within the computing device 600, such as during start-up. The computing device 600 can further include storage devices 660 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. The storage device 660 can include software modules 662, 664, 666 for controlling the processor 620. The system 600 can include other hardware or software modules. The storage device 660 can be connected to the system bus 610 by a drive interface. The drives and the associated computer-readable storage devices can provide nonvolatile storage of computer-readable instructions, data structures, program modules and other data for the computing device 600. In one aspect, a hardware module that performs a particular function can include the software component stored in a tangible computer-readable storage device in connection with the necessary hardware components, such as the processor 620, bus 610, display 670 and the like to carry out a particular function. In another aspect, the system can use a processor and computer-readable storage device to store instructions which, when executed by the processor, cause the processor to perform operations, a method or other specific actions. The basic components and appropriate variations can be modified depending on the type of device, such as whether the device 600 is a small, handheld or portable computing device, a desktop computer, or a computer server. When the processor 620 executes instructions to perform "operations", the processor 620 can perform the operations directly and/or facilitate, direct, or cooperate with another device or component to perform the operations.

Although the exemplary embodiment(s) described herein employs the hard disk 660, other types of computer-readable storage devices which can store data that are accessible by a computer, such as magnetic cassettes, flash memory cards, digital versatile disks (DVDs), cartridges, random access memories (RAMs) 650, read only memory (ROM) 640, a cable containing a bit stream and the like may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 600, an input device 690 represents any number of input mechanisms, such as a microphone for speech, a touch-sensitive screen for gesture or graphical input, keyboard, mouse, motion input, speech and so forth. An output device 670 can also be one or more of a number of output mechanisms known to those of skill in the art. In some instances, multimodal systems enable a user to provide multiple types of input to communicate with the computing device 600. The communications interface 680 generally governs and manages the user input and system output. There is no restriction on operating on any particular hardware arrangement and therefore the basic hardware depicted may easily be substituted for improved hardware or firmware arrangements as they are developed.

For clarity of explanation, the illustrative system embodiment is presented as including individual functional blocks including functional blocks labeled as a "processor" or processor 620. The functions these blocks represent can be provided through the use of either shared or dedicated hardware, including, but not limited to, hardware capable of executing software and hardware, such as a processor 620, that is purpose-built to operate as an equivalent to software executing on a general purpose processor. For example the functions of one or more processors presented in FIG. 6 can be provided by a single shared processor or multiple processors. (Use of the term "processor" should not be construed to refer exclusively to hardware capable of executing software.) Illustrative embodiments can include microprocessor and/or digital signal processor (DSP) hardware, read-only memory (ROM) 640 for storing software performing the operations described below, and random access memory (RAM) 650 for storing results. Very large scale integration (VLSI) hardware embodiments, as well as custom VLSI circuitry in combination with a general purpose DSP circuit, can also be provided.

The logical operations of the various embodiments can be implemented as: (1) a sequence of computer implemented steps, operations, or procedures running on a programmable circuit within a general use computer; (2) a sequence of computer implemented steps, operations, or procedures running on a specific-use programmable circuit; and/or (3) interconnected machine modules or program engines within the programmable circuits. The system 600 shown in FIG. 6 can practice all or part of the recited methods, can be a part of the recited systems, and/or can operate according to instructions in the recited tangible computer-readable storage devices. Such logical operations can be implemented as modules configured to control the processor 620 to perform particular functions according to the programming of the module. For example, FIG. 6 illustrates three modules Mod1 662, Mod2 664, and Mod3 666 that are modules configured to control the processor 620. These modules may be stored on the storage device 660 and loaded into RAM 650 or memory 630 at runtime or may be stored in other computer-readable memory locations.

One or more parts of the example computing device 600, up to and including the entire computing device 600, can be virtualized. For example, a virtual processor can be a software object that executes according to a particular instruction set, even when a physical processor of the same type as the virtual processor is unavailable. A virtualization layer or a virtual "host" can enable virtualized components of one or more different computing devices or device types by translating virtualized operations to actual operations. Ultimately however, virtualized hardware of every type can implemented or executed by some underlying physical hardware. Thus, a virtualization compute layer can operate on top of a physical compute layer. The virtualization compute layer can include one or more of a virtual machine, an overlay network, a hypervisor, virtual switching, and any other virtualization application.

The processor 620 can include all types of processors disclosed herein, including a virtual processor. However, when referring to a virtual processor, the processor 620 can include the software components associated with executing the virtual processor in a virtualization layer and underlying hardware necessary to execute the virtualization layer. The system 600 can include a physical or virtual processor 620 that receives instructions stored in a computer-readable storage device, which cause the processor 620 to perform certain operations. When referring to a virtual processor 620, the system also includes the underlying physical hardware executing the virtual processor 620.

Embodiments within the scope of the present disclosure may also include tangible and/or non-transitory computer-readable storage devices for carrying or having computer-executable instructions or data structures stored thereon. Devices or a storage medium can be part of a system 300 for measuring fluid recovery and the retrieval and processing of the data received by modules of the system. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules can include routines, programs, components, data structures, objects, and the functions inherent in the design of special-purpose processors and so forth that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure can be practiced in network computing environments with many types of computer system configurations, including personal computers, hand-held devices, multi-processor systems, microprocessor-based or programmable consumer electronics, network PCs, minicomputers, mainframe computers, and the like. Embodiments can also be practiced in distributed computing environments where tasks are performed by local and remote processing devices that are linked (either by hardwired links, wireless links, or by a combination thereof) through a communications network. In a distributed computing environment, program modules can be located in both local and remote memory storage devices.

System 300, for example, by way of general computing system 600, can accept one or more inputs from a user. For example, the system 300 can receive inputs where users select incubation times, if desired, at user-defined temperatures, for example, temperatures simulated downhole conditions. The system can also accept inputs from a user to select proppant/rock formation ratios for delivery, sample components to screen, quantities of formation simulation materials, liquids, and crude oil to deliver, and length of time and rcf to spin the multi-well plate arrangement 440 or appropriate vacuum pressure and time to apply the pressure.

The system 300, 600 can also accept inputs from the first and second delivery arrangements 332, 338, flow device 330, monitoring device 364, and detection system 366 to monitor flowthrough volume. The system 300, 600 can include instructions for selecting delivery order based on rock formation type or generalized categorical expectations of rock formation knowledge, for example, shale, etc. The system 300, 600 can also carry out a custom user-defined delivery order. The system 300, 600 can also rank effectiveness of tested components based on predetermined or user-input criteria. The system 300, 600 can generate and output reports and results of a process for evaluating fluid recovery.

An exemplary method 570 for evaluating fluid recovery, which can be carried out by system 300, 600, is now described with reference to FIG. 5. The method begins at step 572 and continues to step 574. In step 574, the processor 620 receives an instruction to deliver column bed materials to a multi-well plate arrangement 440. For example, the first delivery arrangement 332 can deliver precompressed pellets or a loose volume of proppant or mixed proppant and/or rock granules (i.e., formation cuttings) the vessel 412. Control continues to step 576.

In step 576, the processor 620 receives an instruction to deliver liquid materials to the multi-well plate arrangement 440. For example, the second delivery arrangement 338 delivers a predetermined amounts and types of various liquid materials such as, for example, brine, well fresh water, well flowback water, frac fluid base gel, biocides, surfactants, buffers, well crude oil, or the like to one or more wells 412 of the plate arrangement 440. Such delivery of various liquid materials can be achieved via multiple delivery steps or a single delivery step. Control then continues to step 578 where the processor 620 operates the flow device 330 to flow the liquid materials through the column bed. The flow device 330 is as a centrifuge, a micro-centrifuge, or a vacuum apparatus that is operable to flow fluid through one or more spin columns 410. Control continues to step 580.

In step 580, the processor 620 determines the amount of fluid that flow through the bed. For example, the detection system 366 measures flowthrough volume collected by bottom portion 446 of the plate arrangement 440 after centrifugation or vacuum. The monitoring device 364 can monitor progression of liquid through the spin column 410. Control then continues to step 582 where the process ends.

Figure 7:
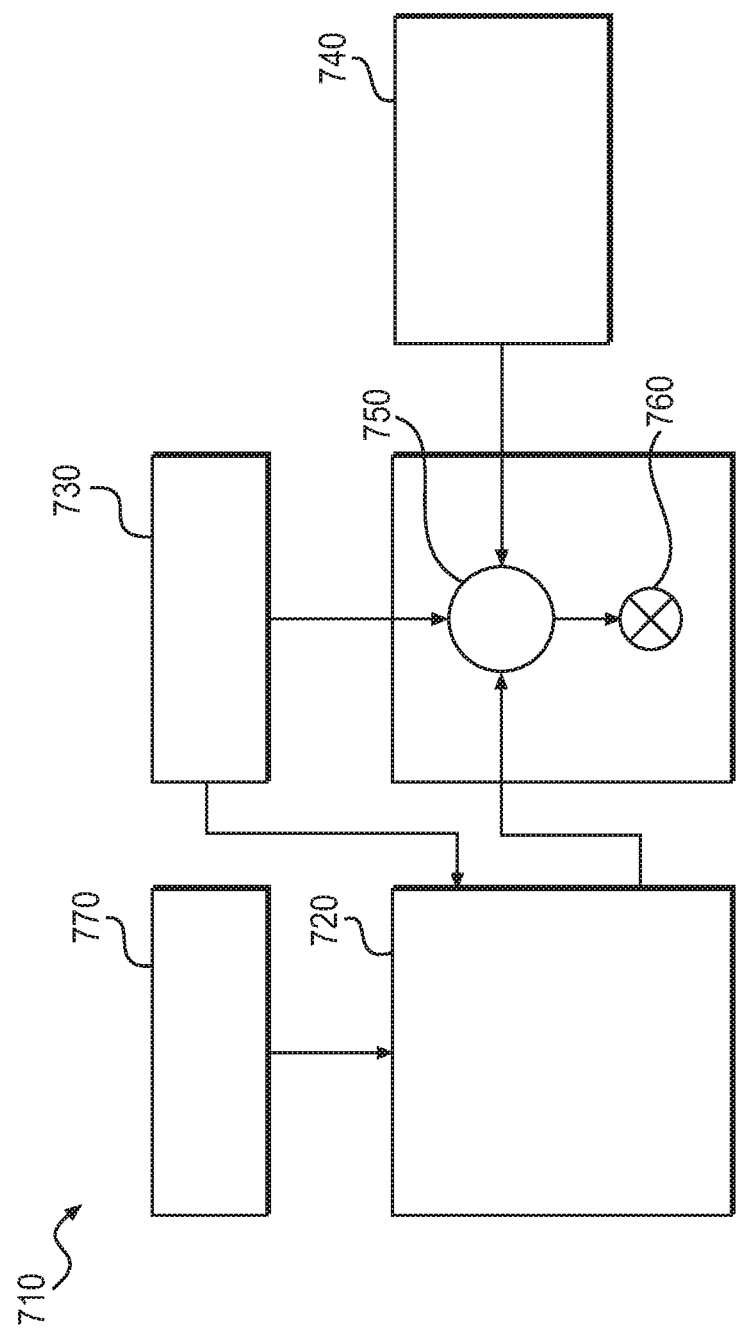
FIG. 7 is a diagram illustrating an example of a fracturing system that may be used in association with certain embodiments of the present disclosure.

The systems and methods for monitoring frac fluid flow through a column bed that are disclosed herein can directly and/or indirectly affect, be affected by and/or be combined with one or more processes, components or pieces of equipment associated with hydraulic fracturing processes, including the preparation, delivery, recapture, recycling, reuse, and/or disposal of fracturing fluids. For example, and with reference to FIG. 7, the disclosed systems and methods may directly or indirectly affect, or be affected by one or more components or pieces of equipment associated with an exemplary fracturing system 710, according to one or more disclosed embodiments. In certain instances, the system 710 includes a fracturing fluid producing apparatus 720, a fluid source 730, a proppant source 740, and a pump and blender system 750 and resides at the surface at a well site where a well 760 is located. In certain instances, the fracturing fluid producing apparatus 720 combines a gel pre-cursor with fluid (e.g., liquid or substantially liquid) from fluid source 730, to produce a hydrated fracturing fluid that is used to fracture the formation. The hydrated fracturing fluid can be a fluid for ready use in a fracture stimulation treatment of the well 760 or a concentrate to which additional fluid is added prior to use in a fracture stimulation of the well 760. In other instances, the fracturing fluid producing apparatus 720 can be omitted and the fracturing fluid sourced directly from the fluid source 730. In certain instances, the fracturing fluid may comprise water, a hydrocarbon fluid, a polymer gel, foam, air, wet gases and/or other fluids.

The proppant source 740 can include a proppant for combination with the fracturing fluid. The system may also include additive source 770 that provides one or more additives (e.g., gelling agents, weighting agents, and/or other optional additives) to alter the properties of the fracturing fluid. For example, the other additives 770 can be included to reduce pumping friction, to reduce or eliminate the fluid's reaction to the geological formation in which the well is formed, to operate as surfactants, and/or to serve other functions.

The pump and blender system 750 receives the fracturing fluid and combines it with other components, including proppant from the proppant source 740 and/or additional fluid from the additives 770. The resulting mixture may be pumped down the well 760 under a pressure sufficient to create or enhance one or more fractures in a subterranean zone, for example, to stimulate production of fluids from the zone. Notably, in certain instances, the fracturing fluid producing apparatus 720, fluid source 730, and/or proppant source 740 may be equipped with one or more metering devices (not shown) to control the flow of fluids, proppants, and/or other compositions to the pumping and blender system 750. Such metering devices may permit the pumping and blender system 750 can source from one, some or all of the different sources at a given time, and may facilitate the preparation of fracturing fluids in accordance with the present disclosure using continuous mixing or "on-the-fly" methods. Thus, for example, the pumping and blender system 750 can provide just fracturing fluid into the well at some times, just proppants at other times, and combinations of those components at yet other times.

Figure 8:
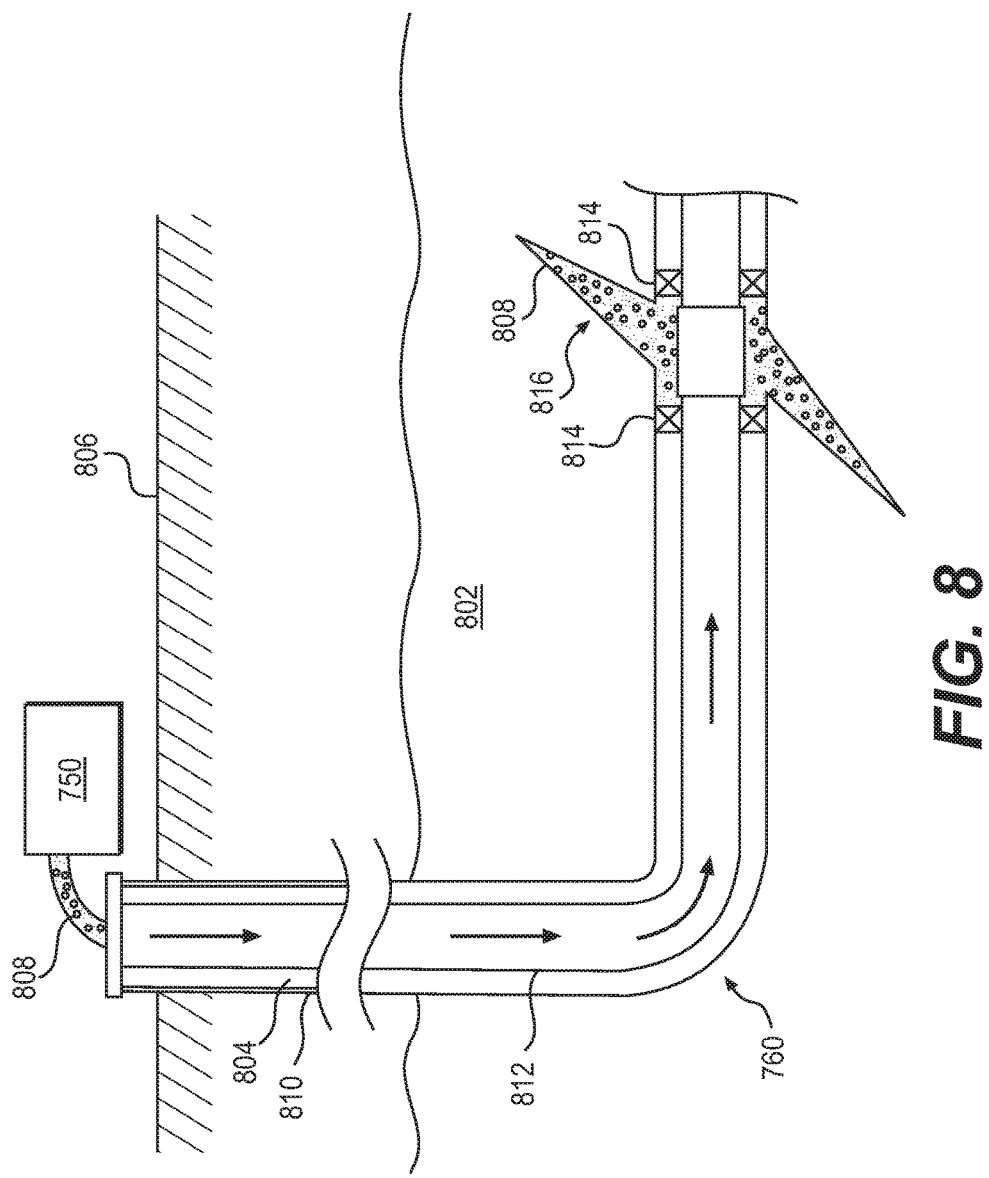
FIG. 8 is a diagram illustrating an example of a subterranean formation in which a fracturing operation may be performed in association with certain embodiments of the present disclosure.

FIG. 8 shows the well 760 during a fracturing operation in a portion of a subterranean formation of interest 802 surrounding a well bore 804. The well bore 804 extends from the surface 806, and the fracturing fluid 808 is applied to a portion of the subterranean formation 802 surrounding the horizontal portion of the well bore. Although shown as vertical deviating to horizontal, the well bore 804 may include horizontal, vertical, slant, curved, and other types of well bore geometries and orientations, and the fracturing treatment may be applied to a subterranean zone surrounding any portion of the well bore. The well bore 804 can include a casing 810 that is cemented or otherwise secured to the well bore wall. The well bore 804 can be uncased or include uncased sections. Perforations can be formed in the casing 810 to allow fracturing fluids and/or other materials to flow into the subterranean formation 802. In cased wells, perforations can be formed using shape charges, a perforating gun, hydro-jetting and/or other tools.

The well is shown with a work string 812 depending from the surface 806 into the well bore 804. The pump and blender system 750 is coupled a work string 812 to pump the fracturing fluid 808 into the well bore 804. The working string 812 may include coiled tubing, jointed pipe, and/or other structures that allow fluid to flow into the well bore 804. The working string 812 can include flow control devices, bypass valves, ports, and or other tools or well devices that control a flow of fluid from the interior of the working string 812 into the subterranean zone 802. For example, the working string 812 may include ports adjacent the well bore wall to communicate the fracturing fluid 808 directly into the subterranean formation 802, and/or the working string 812 may include ports that are spaced apart from the well bore wall to communicate the fracturing fluid 808 into an annulus in the well bore between the working string 812 and the well bore wall.

The working string 812 and/or the well bore 804 may include one or more sets of packers 814 that seal the annulus between the working string 812 and well bore 804 to define an interval of the well bore 804 into which the fracturing fluid 808 will be pumped. FIG. 8 shows two packers 814, one defining an uphole boundary of the interval and one defining the downhole end of the interval. When the fracturing fluid 808 is introduced into well bore 804 (e.g., in FIG. 8, the area of the well bore 804 between packers 814) at a sufficient hydraulic pressure, one or more fractures 816 may be created in the subterranean zone 802. The proppant particulates in the fracturing fluid 808 may enter the fractures 816 where they may remain after the fracturing fluid flows out of the well bore. These proppant particulates may "prop" fractures 816 such that fluids may flow more freely through the fractures 816.

While not specifically illustrated herein, the disclosed methods and compositions may also directly or indirectly affect any transport or delivery equipment used to convey the compositions to the fracturing system 710 such as, for example, any transport vessels, conduits, pipelines, trucks, tubulars, and/or pipes used to fluidically move the compositions from one location to another, any pumps, compressors, or motors used to drive the compositions into motion, any valves or related joints used to regulate the pressure or flow rate of the compositions, and any sensors (i.e., pressure and temperature), gauges, and/or combinations thereof, and the like.

The embodiments shown and described above are only examples. Many details are often found in the art such as the other features of a column flow testing system. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. A method for monitoring frac fluid flow through a column bed, comprising:
   preparing a vessel with a column including a filtering member, a column bed simulating a downhole environment, and a frac fluid;
   flowing the frac fluid through the column bed at an acceleration exceeding gravity for a predetermined period of time; and
   determining the amount of frac fluid recovered after the predetermined period of time,
   adding crude oil, after flowing the frac fluid, to the vessel;
   flowing the crude oil through the column bed; and
   determining one of (i) the amount of crude oil that flows through the column bed and (ii) the ratio of frac fluid to crude oil that flows through the column bed.

2. The method of claim 1, further comprising:
   preparing the vessel further includes adding crude oil, and said flowing the frac fluid includes flowing the frac fluid and the crude oil; and
   determining one of (i) the amount of crude oil that flows through the column bed and (ii) the ratio of frac fluid to crude oil that flows through the column bed.

3. The method of claim 1, wherein flowing of the fluids through the column bed includes centrifuging the vessel.

4. The method of claim 1, wherein flowing of the fluid through the column bed includes applying vacuum pressure.

5. A method for measuring fluid recovery, comprising:
   delivering bed materials to at least one well of a multi-well plate arrangement to prepare a column bed simulating downhole conditions;
   delivering liquid materials to at least one well of the well plate arrangement, the liquid materials including a frac fluid and a crude oil;
   flowing the liquid materials through the column bed at an acceleration that exceeds gravity; and
   determining one of (i) an amount of the liquid materials that flows through the column bed and (ii) the ratio of liquid materials that flow through the column bed
   wherein the crude oil is added to the at least one well of the well plate arrangement after flowing the frac fluid through the column bed.

6. The method of claim 5, wherein said delivering of bed materials includes delivering a first composition of bed materials to a first well of the well plate arrangement and delivering a second composition of bed materials to a second well of the well plate arrangement.

7. The method of claim 6, wherein said delivering of liquid materials includes delivering a first composition of liquid materials to a first well of the well plate arrangement and delivering a second composition of liquid materials to a second well of the well plate arrangement.

8. The method of claim 7, further comprising comparing the amount of the first composition of liquid materials that flows through the column bed of the first well with the amount of the second composition of liquid materials that flows through the column bed of the second well.

9. The method of claim 8, further comprising ranking effectiveness of the first composition of liquid materials and the second composition of liquid materials.

10. The method of claim 6, wherein the delivery of bed materials, the delivery of liquid materials, and the flowing of the liquid materials are based on user inputs.

11. The method of claim 6, further comprising at least one of (i) separating hydrophobic and hydrophilic components of liquid materials that flow through the column bed and (ii) measuring the ratio of hydrophobic and hydrophilic components that flow through the column bed.

12. A system for measuring fluid recovery, comprising:
   a multi-well plate arrangement including a plurality of wells;
   a first delivery arrangement that delivers bed materials to at least one well of the well plate arrangement to prepare a column bed that simulates downhole conditions;
   a second delivery arrangement that delivers liquid materials to the at least one well, the liquid materials including a frac fluid and a crude oil;
   a flow device operably coupled to the well plate arrangement, the flow device being operable to selectively direct flow of the liquid materials through the column bed; and a detector arrangement that measures one of (i) an amount of the liquid materials that flows through the column bed and (ii) the ratio of liquid materials that flow through the column bed, wherein the crude oil is delivered to the at least one well after the frac fluid is flowed through the column bed.

13. The system of claim 12, wherein the second delivery arrangement delivers a first composition of liquid materials to a first well of the well plate arrangement and a second composition of liquid materials to a second well of the well plate arrangement.

14. The system of claim 13, further comprising a processor operably coupled with the detector arrangement, the processor being instructed to compare the amount of the first composition of liquid materials that flows through the column bed of the first well with the amount of the second composition of liquid materials that flows through the column bed of the second well.

15. The system of claim 12, wherein the first delivery arrangement delivers a first composition of bed materials to a first well of the well plate arrangement and a second composition of bed materials to a second well of the well plate arrangement.

16. The method of claim 12, further comprising a processor operably coupled with the first delivery arrangement, the second delivery arrangement, and the flow device, wherein the delivery of the bed materials, the delivery of the liquid materials, and the flowing of the liquid materials are based on user inputs.

17. The system of claim 12, wherein the flow device is one of (i) a centrifuge operable to flow liquid materials through the column bed with a force that exceeds simple gravity and (ii) a vacuum device operable to flow liquid materials through the column bed under vacuum pressure.

18. The system of claim 12, wherein the well plate arrangement includes a first portion that contains the bed materials and liquid materials prior to operation of the flow device, a second portion that sealingly covers a top of the first portion, and a third portion at an end of the arrangement opposite the second portion, wherein the third portion collects flowthrough liquid materials that flow through the column bed by operation of the flow device.

19. The system of claim 18, wherein the well plate arrangement further includes a membrane between the first portion and the third portion, the membrane separating hydrophobic and hydrophilic components of flowthrough liquid.

20. The method of claim 1, wherein the column bed includes a first layer and a second layer.

21. The method of claim 20, wherein the column bed includes a third layer.

* * * * *